United States Patent [19]

Yoshida et al.

[11] Patent Number: 4,882,451

[45] Date of Patent: Nov. 21, 1989

[54] OPTICALLY ACTIVE COMPOUNDS AND PROCESS FOR PRODUCING THEREOF

[75] Inventors: Naoyuki Yoshida, Yokohama; Masakazu Kaneoya; Manabu Uchida, both of Kawasaki, all of Japan

[73] Assignee: Chisso Corporation, Osaka, Japan

[21] Appl. No.: 189,162

[22] Filed: May 2, 1988

[30] Foreign Application Priority Data

May 15, 1987 [JP] Japan ................... 62-116776

[51] Int. Cl.$^4$ ............... C07F 7/08; C07F 7/18
[52] U.S. Cl. ................... 556/440; 556/449; 435/280
[58] Field of Search .................. 556/440, 449

[56] References Cited

U.S. PATENT DOCUMENTS

| 4,189,431 | 2/1980 | Johnson et al. | 556/449 X |
| 4,190,597 | 2/1980 | Floyd et al. | 556/449 X |
| 4,324,729 | 4/1982 | Faukhauser | 556/449 X |

FOREIGN PATENT DOCUMENTS

| 0263987 | 11/1986 | Japan | 556/449 |
| 0175490 | 8/1987 | Japan | 556/449 |
| 0135081 | 2/1961 | U.S.S.R. | 556/449 |
| 0145549 | 6/1962 | U.S.S.R. | 556/449 |
| 0182147 | 7/1966 | U.S.S.R. | 556/449 |

Primary Examiner—Paul F. Shaver
Attorney, Agent, or Firm—Wenderoth, Lind & Ponack

[57] ABSTRACT

The present invention provides optically active compounds and a process for producing the optically active compounds by a biochemical method in which specific compounds having hydroxyl or acyloxy groups are reacted with esters in the presence of hydrolase. The compounds have the following general formula:

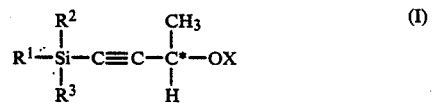

wherein $R^1$, $R^2$ and $R^3$ are selected from alkyl groups having 1-4 carbon atoms and phenyl groups, X is selected from a hydrogen atom and

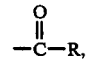

R is selected from alkyl groups having 1-20 carbon atoms, and C* indicates an asymmetric carbon atom.

4 Claims, No Drawings

OPTICALLY ACTIVE COMPOUNDS AND PROCESS FOR PRODUCING THEREOF

BACKGROUND OF THE INVENTION

The present invention relates to optically active compounds which are used as optically active compounds such as physiological active compounds, functional materials and so on, and a process for producing thereof.

Compounds represented by the general formula:

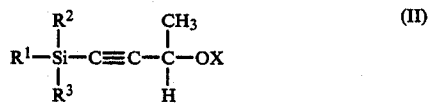

wherein $R^1$, $R^2$ and $R^3$ are selected from alkyl groups having 1–4 carbon atoms and phenyl groups, X is selected from a hydrogen atom

and R is selected from alkyl groups having 1–20 carbon atoms, have not been known as optically active compounds, but as racemates. The compounds represented by the above general formula (II) are useful chemical compounds as starting materials for pharmaceuticals, agricultural chemicals and the like, and as intermediates. However, the compounds have optical isomers, and in many cases they do not sufficiently exhibit their useful characteristics because they are not obtained as pure compounds. Accordingly, it has been required to obtain preponderantly pure R- or S-compounds.

For the above reasons, and in order to obtain an optically active substance, it is necessary to optically resolve a racemate (itself typically obtained by a synthetic chemical technique), to conduct an asymmetric synthesis, or to convert from an optically active starting material by a stereochemical synthetic method. In many cases, the process is troublesome and disadvantageous industrially.

Similar compounds to the above compounds represented by the general formula (II) are synthesized as starting materials of prostaglandin (M. Nishizawa, M. Yamada and R. Noyori, Tetrahedron Letters, 22, 247(1981)). However, alkyl chains of the compounds of the present invention are different from those of the above compounds, so that the optically active compounds of the present invention have not been obtained by the conventional methods.

Accordingly, it is desired to develop a technique for obtaining optically active compounds of the present invention by an industrially advantageous method.

SUMMARY OF THE INVENTION

The inventors of the present invention carried out research for obtaining optically active alcohols and esters thereof by an advantageous industrial method. They found new optically active compounds and a process for producing thereof from racemates represented by the above general formula (II).

Namely, the present invention provides an optically active R- or S-compound represented by the general formula:

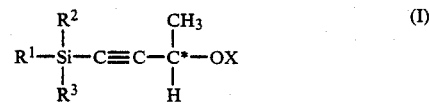

wherein $R^1$, $R^2$ and $R^3$ are selected from alkyl groups having 1–4 carbon atoms and phenyl groups, X is selected from a hydrogen atom and

R is selected from alkyl groups having 1–20 carbon atoms, and C* indicates an asymmetric carbon atom.

The present invention also provides a process for producing optically active compounds represented by the above formula (I) which comprises using a hydrolase, reacting the (R,S)-compound represented by the above formula (II) and an ester to perform a transesterification reaction under substantially anhydrous conditions, and resolving to an optically active compound which contains richly either the R- or S-compound and correspondingly the ester produced from the S- or R-compound.

According to the method of the present invention, the reaction is conducted under anhydrous conditions. This method does not require the use of a small amount of water or a lower alcohol instead of the water, and a side reaction does not occur such as hydrolysis of obtained esters and esters of starting compounds, and formation of undesirable esters, so that the enzyme is stably kept in organic solvent and easily separated after the reaction and re-used. Furthermore, as the enzyme is directly used and reacted in organic solvent, the method can be kept free from contamination by unwanted microorganisms. Accordingly, there is no necessity for preparing special equipment, antiseptics, sterilization treatment, etc. It is possible to conduct the reaction in an open system. Further, the reaction may be conducted in the same or less quantity of solvent in comparison with common organic synthetic reactions in high substrate concentration.

The following description illustrates this invention more specifically.

Compounds used in the present invention are the (R,S)-compounds represented by the above general formula (II). The compounds are characterized by having a triple bond in the formula and available as synthetic substances.

It is also enough to use esters, preferably triglycerides, which are commercially available without any difficulty. Triacetin, tripropionin, tributyrin tristearin, trilaurin, trimyristin, triolein, etc, can be exemplified as the triglycerides. As for other esters, methyl propionate, ethyl butyrate, ethyl stearate, trichloroethyl laurate, butyl laurate, ethylene glycol diacetate, etc, can be used.

The hydrolase which is used in this invention has the ability to catalyze a transesterification reaction preferentially between the R- or S-compound and the ester when the enzyme is used with the (R,S)-compound, and the enzyme can be used regardless its class. For example, a lipase, lipoprotein lipase, esterase, etc., are preferable. The following table shows commercially available enzymes that can be used in the present reaction.

TABLE

| Trade name | Origin | Seller or Maker |
| --- | --- | --- |
| Lipase AP | *Aspergillus niger* | Amano Pharmaceutical Co., Ltd |
| Lipase M | *Mucor javanicus* | Amano Pharmaceutical Co., Ltd |
| Lipase P | *Pseudomonas fluorescens* | Amano Pharmaceutical Co., Ltd |
| Lipase CES | *Pseudomonas sp* | Amano Pharmaceutical Co., Ltd |
| Lipase CE | *Humicola lanuginosa* | Amano Pharmaceutical Co., Ltd |
| Lipase F-AP | *Rhizopus javanicus* | Amano Pharmaceutical Co., Ltd |
| Lipase II | *Porcine pancreas* | Sigma Chemical Co., Ltd |
| Lipase VIII | *Geotrichum candidum* | Sigma Chemical Co., Ltd |
| Lipase X | *Rhizopus delamar* | Sigma Chemical Co., Ltd |
| Lipase | *Chromobacterium viscosum* | Toyo Jozo Co., Ltd |
| Palatase A | *Aspergillus niger* | Novo Industi A/S |
| Lipase | *Rhizopus niveus* | Nagase Biochemicals, Co. Ltd |

In addition to these enzymes, microorganisms which produce the enzymes having the above ability can be used regardless of their species and genus. As such microorganisms, the genera Arthrobacter, Acromobacter, Alcaligenes, Aspergillus, Chromobacterium, Candida, Mucor, Pseudomonas, Rhizopus, etc, can be exemplified. The enzymes produced from these microorganisms can be used also.

In practice of the present invention, (R,S)-alcohols and esters such as triglycerides can be used without any particular treatments.

The reaction is typically conducted by mixing an (R,S)-alcohol with an ester, preferably a triglyceride, if necessary adding an organic solvent such as heptane or toluene when the alcohol is slightly soluble in the ester, and contacting efficiently the mixture with an enzyme.

The reaction temperature is suitably 20° to 70° C. and especially preferably 30° to 45° C. The reaction time is widely variable, say 5 to 2000 hours. The reaction time can be shortened by elevating the reaction temperature or using an enzyme having high activity (large numbers of units) or lowering the substrate concentration.

The (R,S)-alcohol which is a substrate and the ester are suitably mixed in the ratio 1:0.5 to 1:2 by mole, and preferably 1:1.1 to 1:1.5 by mole.

After the transesterification reaction, the enzyme can be removed by conventional filter operation and used again, as it is. The filtrate can be separated into an optically active alcohol and an ester, respectively, for instance by distillation or column chromatography. The obtained ester is hydrolyzed in an alkali or acid solution to derive the optically active alcohol which is an antipode of the above alcohol.

By the above described process, the optically active R- and S-alcohol can be obtained.

When the (R,S)-acyloxy compound is used as substrate instead of (R,S)-alcohol, the same method can be used.

The merits of this invention are as follows.

(1) Unnecessary hydrolysis of esters scarcely occurs because the transesterification reaction is substantially conducted under the conditions of no water.

(2) The enzyme can be easily recovered and re-used.

(3) No special equipment and materials are used because the reaction can be performed under the conditions of relatively lower temperatures and an open system.

(4) Optically active substances having high purity are obtained by a one-step reaction.

(5) In spite of the biochemical reaction, the substrate concentration can be increased and big reaction vessels are unnecessary, because a buffer solution and the like are not required in the reaction.

Using 1-butyne-3-ol as a starting racemate of the present invention, the alcohol is reacted with 3,4-dihydropyran in the presence of pyridinium p-toluenesulfonate and its hydroxy group is protected by tetrahydropyranylation. The protected compound is then trisubstituted sililation by a conventional method. The tetrahydropyranyl group of the product is deprotected by pyridinium p-toluenesulfonate in ethanol and the racemic compound (II) is obtained.

The resulting racemate is optically resolved by the process of the present invention and the compound of the present invention is obtained.

DESCRIPTION OF PREFERRED EMBODIMENTS

The following examples illustrate this invention more specifically, but these will not always be precise in practical applications.

EXAMPLE 1

(i) Production of 3-(2'-tetrahydropyranyloxy)-1-butyne

To a colled solution of 88.6 g of 1-butyne-3-ol and 50 g of 3,4-dihydropyran in 300 ml dichloromethane at 0° C., 200 ml of a dichlorometane solution of 5 g pyridinium p-toluenesulfonate was added dropwise, stirred for one hour under ice-cold conditions, then stirred for one hour at room temperature, and permitted to stand for one night. The solution was cooled in ice, 3 g of sodium bicarbonate was added to the solution. After stirring the solution for one hour, dichloromethane was removed under reduced pressure. 200 ml of heptane was added to the residue and the solution was chromatographed over silica gel. After the solvent was removed, 164.6 g of 3-(2'-tetrahydropyranyloxy)-1-butyne having the boiling point of 50°–51° C./5Torr was obtained by reduced distillation.

(ii) Production of 1-trimethylsilyl-3-(2'-tetrahydropyranyloxy)-1-butyne

To a cooled solution of 80 g of 3-(2'-tetrahydropyranyloxy)-1-butyne in 300 ml of tetrahydrofuran at 10° C., 300 ml of a tetrahydrofuran solution of ethyl magnesium bromide which is prepared from 62 g of bromoethane was added dropwise for one hour. At the conclusion of the addition, the solution was refluxed for 1.5 hours and cooled. To the solution, a solution of 56.5 g of chlorotrimethyl silane in 200 ml of tetrahydrofuran was added dropwise for one hour, and permitted to stand for one night. The solution was cooled and 400 ml of aqueous solution of 55 g of ammonium chloride was added dropwise. The products were extracted with n-heptane. The obtained organic layer was washed with water until it was neutral, and dried. The resulting compounds were concentrated and distilled under reduced pressure. 99 g of 1-trimethylsilyl-3-(2'-tetrahydropyranyloxy)-1-butyne having the boiling point of 93°–95° C./6Torr was obtained.

(iii) Production of (R,S)-1-trimethylsilyl-1-butyne-3-ol

To a solution of 45.3 g of 1-trimethylsilyl-3-(2'-tetrahydropyranyloxy)-1-butyne in 100 ml of ethanol, 2.5 g of pyridinium p-toluenesulfonate was added and stirred for 4.5 hours at 55° C. The reaction mixtures were purified by chromatographed over silica gel under reduced pressure and the solvent was removed. 17.5 g of (R,S)-1-trimethylsilyl-1-butyne-3-ol having the boiling point of 72°–80° C./25Torr was obtained.

(iv) Optical resolution

Ten grammes of enzyme (produced by Amano pharmaceutical Co. Ltd., lipase "Amano CES"), 14.2 g (0.1 mol) of (R,S)-1-trimethylsilyl-1-butyne-3-ol and 28.6 g (0.11 mol) of tripropionin were charged into three-necked flask and reacted with stirring for six days at 35° C. After the reaction was stopped, the enzyme was removed by filtration and the desired compounds were isolated from the filtrate by distillation under reduced pressure. As the result, 6 g of optically active 1-trimethylsilyl-1-butyne-3-ol (rotation $\alpha_D = +1.2°$ (neat, 1 cm cell)) and 1.5 g of optically active 1-trimethylsilyl-1-butyne-3-yl propionate (specific rotation $[\alpha]_D = +59°$ (c1.0, CHCl$_3$)) were obtained.

The obtained compounds were identified by structure analysis with NMR.

EXAMPLE 2

Using the same optical resolution method as used in Example 1, 50 g of lipase "Amano CES", 71 g (0.5 mol) of (R,S)-1-trimethylsilyl-1-butyne-3-ol and 151 g (0.5 mol) of tributyrin were charged into three-necked flask and reacted as described in Example 1. As the result, 25 g (yield 70%) of optically active S-1-trimethylsilyl-1-butyne-3-ol (specific rotation $[\alpha]_D^{26} -19°$(C 4.0, CHCl$_3$) and R-1-trimethylsilyl-1-butyne-3-yl butyrate were obtained.

The obtained compounds were identified by structure analysis with NMR.

To better illustrate the utility of the compounds of the invention, it is pointed out that in the case of certain physiologically active compounds having an asymmetric carbon atom, such as thalidomide (1)

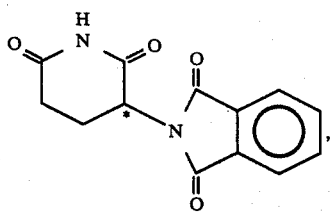

its racemate may have an effect on disease, but one of the isomers may have bad side effects such as causing deformity. Accordingly, it is required to obtain useful racemates and useful R- or S- compounds, respectively.

When one optical isomer, e.g., the R-compound, is required as an end product, the compound can be obtained by stereochemical inversion reaction such as the Mitsunobu reaction (2)

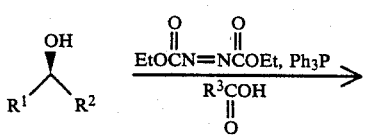

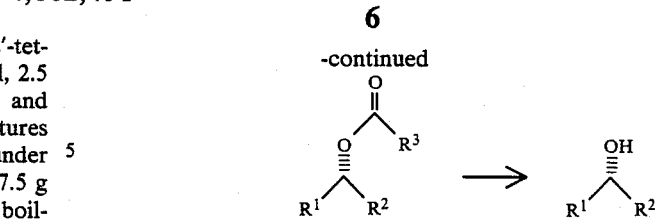

from another optically pure isomer, e.g., the S-compound. Accordingly, each of these isomers, the R- and the S-compounds, is useful as a starting material.

For example, β-ionol (a perfume) of the formula

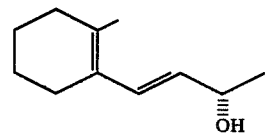

can be obtained by the following synthetic steps in which an E-compound can be selectively obtained by a method (Zweifel et al., J. Org. Chem., 43, 2739 (1978), ibid, 46, 1292 (1981)) from a compound of the present invention and then by a well-known method.

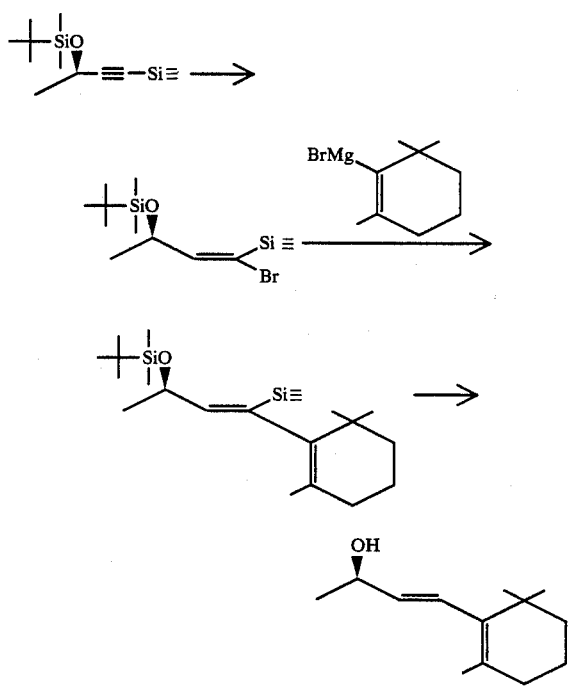

Furthermore, a compound of the present invention can lead to a starting material (III) of a 2-azetidinone derivative (II) which is an intermediate of carbapenem or a penem compound described in Japanese Unexamined Publication No. 61-207373.

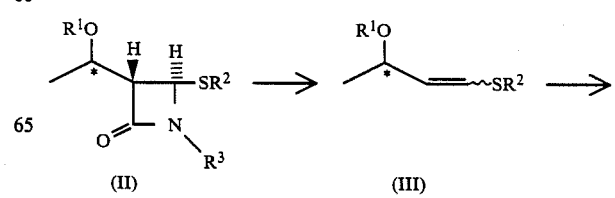

-continued

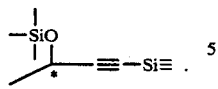

We claim:

1. An optically active R- or S-compound represented by the general formula:

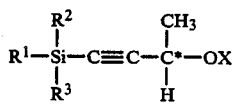

wherein $R^1$, $R^2$ and $R^3$ are selected from alkyl groups having 1–4 carbon atoms and phenyl groups, X is selected from a hydrogen atom and $$-\overset{O}{\underset{\|}{C}}-R,$$

is selected from alkyl groups having 1–20 carbon atoms, and $C^*$ indicates an asymmetric carbon atom.

2. A compound as claimed in claim 1, wherein the compound represented by the formula (I) is optically active 1-trimethylsilyl-1-butyne-3-ol.

3. A compound as claimed in claim 1, wherein the compound represented by the formula (I) is optically active 1-trimethylsilyl-1-butyne-3-yl propionate.

4. A compound as claimed in claim 1, wherein the compound represented by the formula (I) is optically active 1-trimethylsilyl-1-butyne-3-yl butyrate.

* * * * *